United States Patent [19]

Blackwell, III et al.

[11] Patent Number: 4,496,728

[45] Date of Patent: Jan. 29, 1985

[54] METHOD FOR THE PRODUCTION OF 2-ISOPROPYL-4-METHYL-6-HYDROX-YPYRIMIDINE

[75] Inventors: Joseph T. Blackwell, III, Denham Springs, La.; Larry Gasper, III, Greensboro, N.C.

[73] Assignee: Ciba-Geigy Corporation, New York, N.Y.

[21] Appl. No.: 419,842

[22] Filed: Sep. 20, 1982

[51] Int. Cl.$^3$ .......................................... C07D 239/36
[52] U.S. Cl. ..................................................... 544/319
[58] Field of Search ........................................ 544/319

[56] References Cited

U.S. PATENT DOCUMENTS 4,014,879 3/1977 Bulke ................................... 544/319
4,308,258 12/1981 Okabe ................................. 424/200

Primary Examiner—Robert Gerstl
Attorney, Agent, or Firm—Karl F. Jorda

[57] ABSTRACT

A process is described for the production of 2-isopropyl-4-methyl-6-hydroxypyrimidine (oxypyrimidine) by reacting isopropylamidine in an alkaline lower alkanol solvent system with an alkyl acetoacetate to close the ring and form the oxypyrimidine in a continuous flow multi-stage reactor (MSR) under controlled multi-stage conditions whereby the reactants contact each other in each of said stages under conditions which reduce the possibility of the formation of unwanted reaction products from said reactants in said solvent system.

8 Claims, No Drawings

METHOD FOR THE PRODUCTION OF 2-ISOPROPYL-4-METHYL-6-HYDROXYPYRIMIDINE

FIELD OF THE INVENTION

The present invention relates to an improved continuous process for the preparation of 1-isopropyl-4-methyl-6-hydroxypyrimidine (oxypyrimidine), a useful intermediate. More particularly, it relates to an improved process providing higher yields of oxypyrimidine by improved continuous multi-stage reaction of the starting materials with each other. The process is also useful in the preparation of the cyclopropyl homolog, which is also a useful intermediate.

BACKGROUND OF THE INVENTION

Oxypyrimidine is an important precursor in the manufacture of a class of thioesters of oxypyrimidine which have insecticidal and acaricidal activity as disclosed in U.S. Pat. No. 2,754,243. One of these compounds, O,O-diethyl-O-(2-isopropyl-4-methyl-6-pyrimidyl) thiophosphate is well-established commercial product under the trademark DIAZINON ®. As the product is manufactured and sold in large quantities, each improvement in the manufacture of oxypyrimidine is of economic importance. While the discussions which follow are primarily directed to the 2-isopropyl embodiment they also apply to its 2-cyclopropyl homolog which is also a precursor for insecticidal compounds.

The n-propyl homolog reacts similarly.

Oxypyrimidine presently is synthesized by way of three reaction steps (Equations I, II, III):

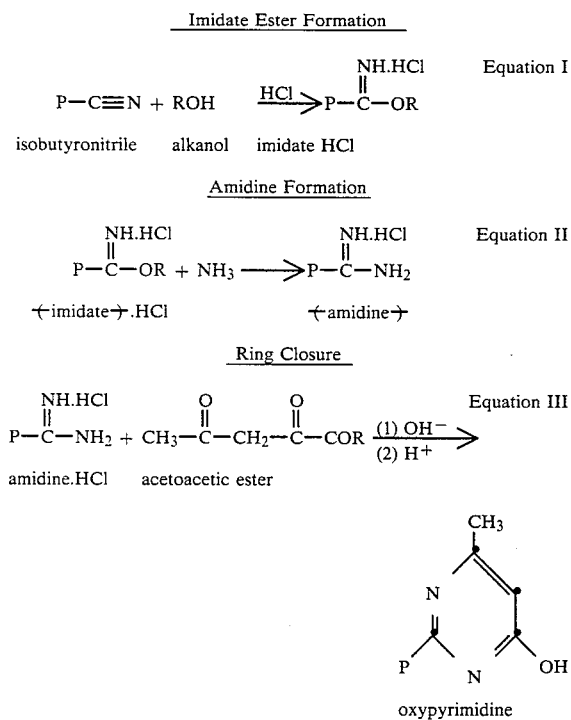

Equations I and II above are optimized by the solvents and conditions taught in U.S. Pat. No. 4,111,976.

In the search for more economical processes for the manufacture of oxypyrimidine various expedients have been proposed such as the optimized ring closure disclosed in U.S. Pat. No. 4,014,879. The reaction is initiated in a single vessel in aqueous alkali as the solvent medium and completed and polished in a subsequent vessel. To achieve commercial yields excesses of 30 to 35% methylacetoacetate are required.

Utilizing water as the sole reaction solvent required a large excess of acetoacetic acid ester, preferably about 30 to 35% excess of methyl acetoacetate (MAA). The excess MAA was required because of competing hydrolysis side reactions. Attempts were made to reduce the required 30 to 35% excess of MAA by using water-insoluble solvents with or without phase-transfer catalysts. It was postulated that the MAA would distribute primarily in the organic solvent and would be protected from hydrolysis. Diketene was also used in the two-phase system to see if it could be substituted for MAA.

In practice it was found that the introduction of a two-phase solvent system (solvents used were toluene and isopropyl ether) made no difference in yield. The water-immiscible solvent had little positive or negative effect on the reaction. It was believed that the reaction took place entirely in the aqueous phase and that all reactants were present initially in the aqueous phase.

The required excess of methylacetoacetate has been reduced to about 5 mole % by the invention of U.S. patent application Ser. No. 368,771, filed Apr. 15, 1982 and commonly assigned. The aqueous alkali reaction medium is modified by replacing all or most of the water with a lower alkanol. Yields of 80 to 85% are obtained with this reduced methylacetoacetate excess in a stirred continuous flow reactor.

As stated above, U.S. patent application Ser. No. 368,771 utilizes a lower alkanol, specifically, methanol or ethanol to provide a commercially variable reaction scheme. This is an extension of the process of U.S. Pat. No. 4,111,976 wherein the amidine is formed in the presence of a lower alkanol (methanol or ethanol) as the reaction medium.

However, the three-stage procedure of Equations I, II and III, mentioned above, was still preferred, especially after the first stage reaction was optimized in accordance with the procedure of U.S. Pat. No. 4,111,976 and Ser. No. 368,771 wherein methyliminoisobutyrate hydrochloride was prepared by reacting isobutyronitrile (IBN), hydrogen chloride (HCl) and methanol (MeOH) in methanolic solution continuously containing an excess of HCl.

The second and third stages were carried out using methanolic water as the reaction solvent for the amidine formation (Equation I) and methanol as in Ser. No. 368,771 for the ring closure (Equation III).

It was believed that the methanolic solution reduced the rate of the two competing hydrolysis reactions, IV and V which occurred during the ring closure reaction of Equation III.

The three reactions simultaneously occuring in parallel are:

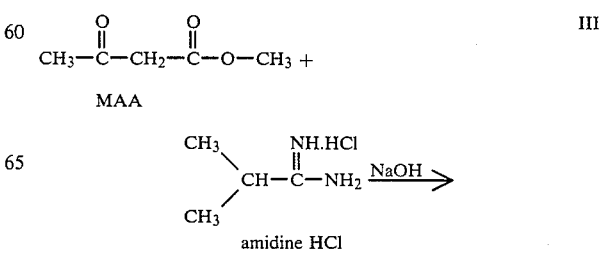

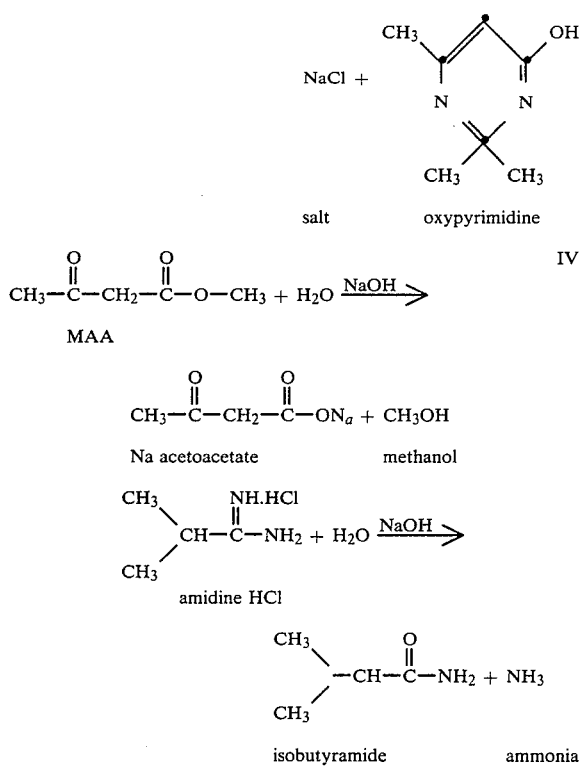

The hydrolysis of MAA and amidine.HCl is highly undesirable as these are expensive raw materials and the requirements for oxypyrimidine run to about 10 million pounds per year.

In order to effect proper economies, the three concurrent reactions, via their kinetics were studied.

An examination of the kinetics of the three reactions indicates that the ring closure oxypyrimidine formation (Equation III) is second order, i.e., dependent upon the concentrations of both MAA and amidine.HCl, while both MAA hydrolysis and amidine.HCl hydrolysis, (Equations IV and V) are pseudo-first order, i.e., dependent only on the concentration of MAA or amidine.HCl, because the concentration of $H_2O$ present in the NaOH will be much greater than either reactant. This dictates then that for minimum hydrolysis of MA and amidine. HCl, and, therefore, for maximum yield of oxypyrimidine, the contact between MAA, amidine.HCl, and $NaOH/H_2O$ at high pH should be kept to a minimum.

It is also noted that by replacing most of the water with methanol, the reaction rate of the ring closure of Equation III was halved but the reaction rate of the hydrolysis of Equation IV and V were seen further reduced (about ⅓ to 1/5).

In a constant flow stired tank rector, the minimal contact between nascent reactants is difficult to maintain because the vessel contents are being constantly and turbulantly mixed with the incoming raw materials. However, in a plug flow reactor having concurrent progressive flow the contents are constantly moving away from the incoming raw materials, thereby minimizing hydrolysis losses and maximizing oxypyrimidine yield.

However, plug flow reactors commonly used in continuous flow reaction unit operations, are difficult to use when the reaction products or by-products contain solids. A close approximation to such plug flow reactors is the multi-stage reactor (MSR) comprising a series of chambers (stages) connected by restricted flow orifices to ensure limited dwell time for the reactants at each stage but preventing back mixing of the incoming raw materials, ensuring constant controlled movement of the reaction contents away from the incoming raw materials.

THE INVENTION

This invention resides in the process for reacting an amidine of the formula

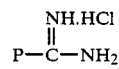

where p is propyl, isopropyl, or cyclopropyl with an alkyl acetoacetate of the formula

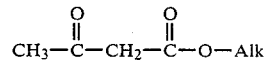

where Alk is methyl or ethyl to effect ring closure under alkaline conditions which comprises the steps of continuously introducing into the first stage vessel of a multi-stage reactor, the amidine, a slight stoichiometric excess of the acetoacetate and a methanolic solution of alkali metal hydroxide at pH above 11 and at temperatures below 25° C., flowing the reaction contents from said first stage away from the zones of raw material introduction into the second stage vessel with concommitant cooling to 40° C.±5° C. and pH maintainance to 12.0±1 (preferably, 12.0±0.2) to initiate the ring closure reaction; then subsequently flowing of said contents with minimum turbulence into further stage vessels at said pH and temperatures until the ring-closure reaction is substantially complete; and then flowing said MSR contents into at least one polishing vessel to ensure completion of the reaction. Distillation for recovery of the alkanol and isolation of the final slurry of the oxypyrimidine and salt follow.

DETAILED DESCRIPTION OF THE INVENTION

While the invention will be described with reference to industrial manufacture under continuous conditions of millions of pounds annually of oxypyrimidine, under laboratory conditions in analogous apparatus, equivalent yields and improvements can be obtained with the cyclopropyl and n-propyl embodiments.

The preferred alkyl acetoacetate is methyl acetoacetate as it is available in tank car lots. The ethyl acetoacetate while useful, costs more and recovery of ethyl alcohol, a taxable item, requires special safeguards, accounting and other well-recognized complications.

The preferred alkanol for the reaction medium is methanol. It sufficiently slows down the reaction rate to permit ring closure within a reasonable reaction time in the multi-stage reactor without undue hydrolysis of the raw material reactants. While ethanol additionally slows down all the reaction rates involved, it does so at the expense of an inordinate extension of the reaction time, thus requiring either addition stages or larger individual vessels at each stage to ensure completion of the reaction and sufficient throughput to meet annual production requirements with minimal capital investment for industrial scale equipment.

As discussed above, the oxypyrimidine reaction kinetics indicate a batch reactor or a plug flow reactor will give optimum yields. Of these two, the plug flow reactor is favored because it both gives maximum yield per unit volume and avoids problems of batch to batch variation.

But a plug flow reactor cannot be used directly for the oxypyrimidine ring closure reaction (Equation III) because of the problem of handling the solid NaCl that is produced. However, it can be closely approximated using a multi-stage reactor with a sufficient number of stages.

In the laboratory as well as on an industrial scale the multi-stage reactor should include at least five and preferably ten individual chambers of approximately equal volumes. The size of the individual chambers is controlled together with the feed flow rates to provide a minimum residence time per chamber and stage of about 2-8, preferably five, minutes. The initial stage chambers may be sized for minimum residence time and the subsequent chambers slightly expanded to ensure completion of the reaction after the volume of raw reactant materials subject to hydrolysis is sufficiently reduced. However lab considerations show no appreciable advantage for introducing such design complications. The amidine HCl is neutralized and its heat of neutralization removed before its introduction into the MSR as a neutralized amidine solution in methanol. (Some methanol is derived from the preparation of the amidine HCl.) This neutralized amidine solution contains NaCL. It is cooled by circulating through a conventional heat exchanger. To reduce the risk of hydrolysis, the temperature is controlled to 0°-5° C. The cold neutralized amidine is introduced into the first stage of the MSR reactor via a flow controller, as is the methyl acetoacetate, in about 12% stoichiometric excess, at or below room temperature.

The rate of feed of the amidine and MAA to the reactor train, starting at the first stage, is adjusted so that the total residence time in the MSR should be at least 30 minutes with 50 minutes being preferred. After 50 minutes, the ring closure reaction is substantially complete but completion is assured by holding the exiting mixture, overflowing from the MSR, in a stirred polishing tank for at least an additional 30 minutes to two hours.

The second stage of the MSR is provided with a source of caustic (NaOH 50%) to ensure that the amidine-MAA mixture is adjusted to pH 12.0. This pH control throughout the MSR is critical to initiate and to permit the ring closure to proceed. Additional caustic is added during subsequent stages to maintain this parameter at this optimum level. In the laboratory and industrial ten-stage reactors, additional caustic is introduced at about the fifth or sixth stages.

Kinetic analysis has shown that a ten-stage reactor most approximates a continuous plug flow reactor in theoretical and actual yields.

As the ring closure reaction (Equation III) is exothermic, cooling in the ten-stage MSR is applied to stages two, three, six and seven to maintain the temperatures within each stage below about 43° C. and preferably at about 40° C. Polishing tanks, where the reaction is completed and from which the methanol may be recycled, are maintained at 41°-43° C. and pH 12.0±0.2. Holding time is about one hour.

Water is added to the Polishing tanks to maintain solution of the NaCl. The water introduction is controlled at a rate which just dissolves all the salt. The reaction mass is then fed to a stripper column for removal of the methanol and any trace ammonia which may result from any small amount of amidine hydrolysis (Equation V).

After stripping the methanol, the resultant sodium oxypyrimidine reaction mixture is cooled and fed to a neutralizer vessel continuously maintained at pH 6-6.5 by adding 32% HCl. The resulting neutralized slurry of salt and oxypyrimidine is appropriately cooled to below about 10° C., held at this temperature to allow crystal growth in the oxypyrimidine/salt mixture and then filtered and dried. The dried material assays 85% oxypyrimidine, 14% NaCl and traces of water.

In the following examples, a comparison is made between the previously described procedure for continuous synthesis of oxypyrimidine utilizing constant flow stirred tank reactors (CFSTR) described in Example 1 with results obtained on the laboratory MSR mode (Example 2) and on pilot scale MSR (Example 3), utilizing the novel concept of the MSR for handling the slurried product. In the laboratory apparatus the methylacetoacetate was fed into the first stage reactor at a rate of 1.05 mol/hour. This is 5% excess of MAA based on the calculated amount of synthesized amidine present in the reaction mixture from reaction I and II starting with the isobutyronitrile via the methylimonoether (MIE). Using the 5% MAA excess in the laboratory MSR, the yield of oxypyrimidine was 88-90%.

In the industrial scale MSR, it was found that yields are best using a 12% molar excess of methyl acetoacetate based on the amidine feed.

The oxypyrimidine yield on this scale is 95% in the reactor slurry and 93.3% in the dried product. The difference between the yields in the reactor slurry and the dried product is based on a 1.7% yield lost in the filtrate.

During optimization runs on the industrial scale MSR, it was found that an increase in MAA may increase the yield slightly but the cost increases. Decreasing MAA by 3% costs a 2% yield loss.

Residence time in the MSR is less sensitive; a 25% time decrease, to 36 minutes causes a one to two % yield decrease.

Temperature and pH should be maintained aa close as possible since either an increase or decrease causes yield to drop. A five degree temperature error is either direction from the 40° C. optimum costs one to two percent yield loss. A ten degree variation costs three to 5% yield. Lower temperatures reduces the amidine conversion and higher temperatures speed hydrolysis of both amidine and MAA.

Errors in pH measurement are the most costly. An error of one pH unit from the pH 12.0 optimum, causes a yield loss of seven to ten percent; even a 0.5 unit error can cost three to four percent. Low pH quenches the reaction and high pH causes increased hydroxylsis.

The following examples illustrate comparative aspects of the prior art, Example 1, and this invention in the laboratory mode, Example 2, as well as a preferred pilot plant mode, Example 3. While the described mode, of Example 3, is presently preferred, the example is illustrative and not intended to be limitative.

EXAMPLE 1

Utilization of Constant Flow Stirred Tank Reactors (CFSTR)

The apparatus for this mode included two 2000 ml. CFSTR's in series, equipped with all necessary pumps, temperature and pH instrumentation, etc. The first CFSTR is filled with 200 ml CH$_3$OH and the temperature adjusted to 40° C.–45° C. Then, Amidine.HCl solution is metered to the first CFSTR at a rate of 1.0 mole/hour, and MAA likewise at a rate of 1.05 moles/hour. 50% NaOH solution was added at a rate such to maintain the pH at 11.5–11.8. Residence time was 45 minutes, after which the contents overflowed to the second CFSTR, where the temperature was maintained at 40° C.–45° C., the pH at 11.5–11.8, and the residence time was likewise 45 minutes.

The reaction product was worked up by distilling off the methanol, neutralizing the residue, and collecting the oxypyrimidine by filtration. The yield of total oxypyrimidine was 83–85%.

EXAMPLE 2

Utilization of a Multi-Stage Reactor (MSR)

The multi-stage reactor (MSR) apparatus for the production of oxypyrimidine via a continuous mode consisted of three distinct units: (1) upstream of the MSR was a cooling circulation loop consisting of a small continuously stirred tank reactor (CSTR), a heat exchanger for cooling the reactor, and a circulating pump; (2) the MSR itself; and (3) downstream of the MSR, another, larger "polishing" CSTR. Each unit was equipped with appropriate temperature and pH instrumentation and associated feeds.

In operation, the reactants were fed to the cooling loop CSTR via metering pumps. The reaction mixture overflowed the cooling loop to the MSR, which in turn overflowed to the polishing CSTR. The product exited the polishing CSTR after an appropriate hold time.

The cooling loop and first stage of the MSR were charged with methanol. The contents were circulated through the heat exchanger, and the temperature was adjusted to 5° C. Then the amidine hydrochloride reaction mixture was metered to the cooling loop at a rate of 1.0 mole/hour, methyl acetoacetate (MAA) at a rate of 1.05 mole/hour (5% excess), and 50% caustic at a rate sufficient to maintain the pH at 11.5–11.8 and then fed to the first stage of the MSR.

The temperature profile in the MSR was maintained at 39°–45° C., and the pH in the MSR was maintained at 11.3–12.0 by further addition of 50% caustic to the second stage. The temperature in the polishing CSTR was maintained at 42° C., and pH at 11.5–11.8; residence time in the polishing CSTR was 1.0 hour.

The reaction product was distilled, neutralized, and filtered as in Example 1. The yield of oxypyrimidine was 88–90%.

EXAMPLE 3

The pilot scale apparatus included a 10 gallon monel ® continuously stirred tank reactor (CSTR) operated at 2–5% to level from an amidine.HCl 70 gal. feed vessel. The multi-stage reactor (MSR) was a 10 gallon glass vessel divided into 10 stages of 1 gallon each. Each stage is equipped with agitators. Between each stage there was 1 3/16 inch diameter transfer hole. Stage 1 was equipped for the introduction of MAA and the neutralized amidine. Stages 2 and 6 were provided with caustic feed piping and requisite pH measurement sensors for controlling the caustic feed. Stages 2 and 3 had internal coils for cooling water. This design and the pump rates were adjusted to provide a residence time at each stage of about 5 minutes. The flow rate was about 0.20 gallons/minute. The effluent from the MSR was fed to the polishing reactors, two 10 gallon agitator equipped monel ® tanks in series utilized at the 90–100% level, to provide a holding time of about 100 minutes. The reaction mixture was fed from the last polishing tank through the in line mixer where it was mixed with water to dissolve NaCl, to a stainless steel dist. column to strip methanol from the rxn mass.

The amidine.HCl solution containing methanol was fed to the neutralizer vessel at a rate of 66.7 lbs/hr. together with 8.2 lbs/hr. of 50% sodium hydroxide. The neutralizer effluent was cooled to 2° C. before introduction into the MSR. This also provides a feed of 4.6 gal/hr. of methanol. The cascade level control in the 10 gal. neutralizer was set at about 1.0 gallon to control the effluent rate to properly fix the flow of the amidine solution to the MSR first stage at 8.4 gal/hr. To the MSR first stage was continuously fed 1.76 gal/hr. of methylacetoacetate 100%.

Stage 2 pH control was set at pH 12.0. This provided a feed of 0.77 gal/hr. of 50% NaOH at this second stage. The temperature controller at stages 2 and 3, were set at 40° C. in conjunction with the cooling coils at these stages. The pH controller at stage 6 was set at pH 12 and provided a flow of 50% NaOH of 0.20 gal/hr. Ring closure to oxypyrimidine in the MSR efluent stream was about 93–95% going to the first Polishing CSTR.

The Polishing CSTR controllers were set to pH 12 (Requiring an NaOH feed of about 0.02/gal hr.) and 41°–43° C. The ring closure was 95% complete to oxypyrimidine in the Polishing CSTR.

After polishing, the flow was diluted with water, then transferred at pH 12 into a distillation holding tank. During the transfer 5.5 gal/hr. of water was introduced into the slurry to dissolve all the salt. The feed from the holding tank to the methanol distillation stripper was 17.5 gal/hr. The overhead temperature during the distillation was near 65° C. and the reboiler temperature was about 105° C. This provided 5.7 gal/hr. of distillate. This distillate was neutralized with H$_2$SO$_4$ (0.05 gal/hr.) to pH 6.5.

The stripping column bottoms solution (11.1 gal/hr.) was cooled and fed to a stirred neutralizer vessel. The solution was neutralized to pH 6.5 by 32% HCl (1.6 gal/hr). The temperature was permitted to rise adiabatically and stabilized at about 40°–50° C. The level control at the neutralizer was set to flow the slurry to a scraped surface heat exchanger to cool it to less than 5° C. and from there to a filter where 17.3 lbs/hr of oxypyrimidine (as 100%) was collected.

As stated supra this provides a 95% total yield (based on isobutyronitrile) of oxypyrimidine. This is recovered as an 85% mixture with 14.7% NaCl and up to 0.3% moisture.

What is claimed is:

1. A process for preparing an oxypyrimidine-type compound of the formula:

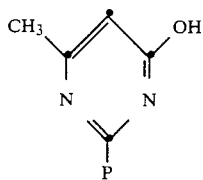

where P is selected from the group consisting of isopropyl, cyclopropyl and n-propyl-, which comprises the steps of reacting an amidine hydrochloride of the formula:

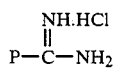

with an acetoacetic ester of the formula:

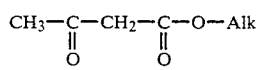

where Alk is methyl or ethyl, to effect ring closure by introducing an alkali-neutralized methanolic solution of said amidine hydrochloride to a temperature range of −5° C. to 15° C. together with said acetoacetic ester into the first stage of a multi-stage reactor, this multi-stage reactor comprising a series of chambers (stages) connected by restricted flow orifices to ensure limited dwell time for the reactants at each stage but preventing back mixing of the incoming raw materials, flowing said mixture of reactants into the second stage of said multi-stage reactor away from the zone of reactant introduction; adjusting the pH in said second stage to 12.0±1 with caustic solution to initiate said ring closure reaction while maintaining a temperature in said second stage at 40°±5° C.; flowing said reaction mixture maintained at said temperature and pH to at least one successive stage; holding said reaction mixture of each of said successive stages for at least 2–8 minutes until the ring closure reaction at the last stage is complete.

2. The process according to claim 1 where the oxypyrimidine-type compound is 2-isopropyl-4-methyl-6-hydroxypyrimidine.

3. The process according to claim 2 wherein said neutralized methanolic amidine solution is introduced into the first stage of said multi-stage reactor at a temperature of about 0°–5° C.

4. The process according to claim 2 wherein said multi-stage reactor contains ten stages.

5. The process according to claim 4 wherein the holding time at each of the stages of said multi-stage reactor is 5 minutes to a total reaction time in said multi-stage reactor of about 50 minutes.

6. The process according to claim 2 wherein said last stage is carried out in a polishing holding tank at pH 12.0±1.0 and 40°–45° C. until said reaction is completed.

7. The process according to claim 6 wherein the holding time in said polishing tank is at least one hour.

8. The process according to claim 2 wherein the temperature in said second stage is maintained at 40°±2° C.

* * * * *